United States Patent
Oevering et al.

(10) Patent No.: US 6,175,036 B1
(45) Date of Patent: Jan. 16, 2001

(54) PROCESS TO PREPARE A PENTENOIC ACID DERIVATIVE

(75) Inventors: Henk Oevering, Stein (NL); Patrick M Burke, Wilmington, DE (US); Otto E Sielcken, Sittard (NL)

(73) Assignee: DSM N.V., Heerleen (NL)

( * ) Notice: Under 35 U.S.C. 154(b), the term of this patent shall be extended for 0 days.

(21) Appl. No.: 09/384,060

(22) Filed: Aug. 26, 1999

Related U.S. Application Data

(62) Division of application No. 08/805,829, filed on Feb. 26, 1997, now abandoned.
(51) Int. Cl.⁷ .................................................. C07C 67/36
(52) U.S. Cl. .......................................... 560/207; 560/130
(58) Field of Search ...................................... 560/207, 130

(56) References Cited

U.S. PATENT DOCUMENTS 5,495,041 * 2/1996 Sielcken et al. .

FOREIGN PATENT DOCUMENTS

95/06027 * 3/1995 (WO) .
96/29300 * 9/1996 (WO) .

* cited by examiner

Primary Examiner—Paul J. Killos
(74) Attorney, Agent, or Firm—Pillsbury Madison & Sutro Intellectual Property Group

(57) ABSTRACT

Process for the preparation of an alkyl pentenoate respectively an aryl pentenoate by contacting an alkoxy-butene respectively an aryloxy-butene compound with carbon monoxide in the presence of a catalyst system comprising palladium, a phosphorus ligand and an acid promotor, wherein the molar ratio of 3-alkoxy-1-butene to 1-alkoxy-2-butene, respectively the molar ratio of 3-aryloxy-1-butene to 1-aryloxy-2-butene, is higher than 4.

18 Claims, No Drawings

PROCESS TO PREPARE A PENTENOIC ACID DERIVATIVE

This application is a Division of Ser. No. 08/805,829 filed Feb. 26, 1997 now abandoned.

The invention relates to a process for the preparation of an alkyl pentenoate respectively an aryl pentenoate by contacting an alkoxy-butene respectively an aryloxy-butene with carbon monoxide in the presence of a catalyst system comprising palladium, a phosphorus ligand and an acid promotor.

Such a process is described for the preparation of an alkyl pentenoate ester in WO-A-9629300. This patent application describes the carbonylation reaction of a mixture of 3-methoxy-1-butene and 1-methoxy-2-butene in a molar ratio of 1.1 with carbon monoxide in the presence of a catalyst system comprising a palladium compound, a phosphine ligand and an acid promotor. The yield reported to methyl pentenoate was 63% after 5 hours, using a catalyst system consisting of $PdCl_2$, diphenylphosphinopyridine and para-toluene sulphonic acid.

A disadvantage of this process is that the rate of the carbonylation reaction is relatively low. Furthermore the yield to the pentenoate compound needs to be improved in order to make this process more attractive for commercial use on a large scale.

The object of this invention is to provide a process for the preparation of a pentenoate compound starting from alkoxy butene or aryloxy butene, in which the rate of the reaction and the selectivity to the pentenoate compound are improved.

This object is achieved in that the molar ratio of 3-alkoxy-1-butene to 1-alkoxy-2-butene, respectively the molar ratio of 3-aryloxy-1-butene to 1-aryloxy-2-butene, is higher than 4.

It was found that the rate of the reaction of the process according to the invention is significantly higher than the rate of the reaction disclosed in WO-A-9629300. Furthermore the selectivity to the 3-pentenoate compound is significantly improved. Another advantage is that the process can be performed at a lower temperature, because of the higher rate of reaction. High temperatures result in degradation of the phosphine ligand. Consequently the rate of consumption of the phosphine ligand per kg of pentenoic acid derivative is lower when using the process according to the invention at lower temperatures.

A further advantage is that these improved results can be achieved in a process in which no or only a slight amount of halogen compounds are present. Furthermore the process according to the invention does not have to make use of the strong acids as disclosed in WO-A-9629300. Good results can be achieved using weak acids. The fact that the process can be performed in the absence of halogens and/or strong acids can be regarded as a major advantage.

Another advantage is that the selectivity to the 2-pentenoic acid derivative isomer is lower than when the state of the art process is used. This is, for example, advantageous when the mixture of isomers is used as starting compound in the hydroformylation reaction to 5-formylvalerate starting from mixture of isomers of pentenoate esters. The 2-pentenoate ester result in undesirable side reactions in the hydroformylation and lowering the amount of 2-pentenoate ester results in a lower by-product formation in the hydroformylation. This is for example illustrated in WO-A-9506027.

The alkoxy and aryloxy group may be a $C_1$–$C_{20}$ alkoxy and a $C_6$–$C_{20}$ aryloxy group respectively. These groups may be substituted. The alkoxybutenes and aryloxybutenes can be presented by the following formula's:

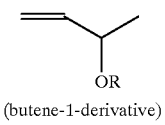

(butene-1-derivative) (1)

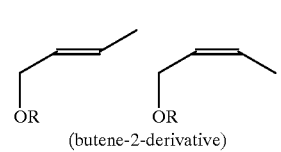

(butene-2-derivative) (2)

in which R is preferably an aliphatic, cyclo-aliphatic or aromatic group. Examples of possible RO-groups having an aromatic group $R^1$ are phenyl, cresyl, xylenyl or naphthyl. Most preferred is phenyl. Preferably alkyl pentenoates are prepared by the process according to the invention, wherein R is an alkyl group having 1–20 carbon atoms. Examples of possible alkyl groups are methyl, ethyl, isopropyl, n-propyl, n-butyl, octyl, 2-ethylhexyl, 2-propylheptyl, iso-nonyl, decyl or benzyl. Most preferably methyl or ethyl are used because the resulting methyl or ethyl pentenoate can be easily handled, because of their low boiling point. Furthermore these compounds can be advantageously used as precursors in other processes, e.g. to prepare E-caprolactam or adipic acid as described in for example WO-A-9519331 or EP-A-662467.

It was found to be essential to perform the process of the present invention at the claimed ratio of butene-1-derivative relative to butene-2-derivative. In this manner higher reaction rates are achieved. Preferably the amount of butene-1-derivative relative to the total amount of butene derivatives in the starting composition is higher than 80% and more preferably higher than 95%. Lower consumption of catalyst system per kg product is observed when performing the process according to the invention within these ranges.

The reaction is performed using a catalyst system comprising palladium, a phosphorus ligand and an acid promotor.

The phosphorus ligand can be the ligands as described in WO-A-9629300, which patent application is hereby incorporated by reference. Preferably the ligand is a monodentate or multidentate phosphine ligand. The monodentate phosphine ligand can be described by the following general formula:

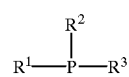

(3)

wherein $R^1$, $R^2$ and $R^3$ each individually represent an optionally substituted organic group. This organic group can be a $C_1$–$C_{20}$ alkyl group, a $C_6$–$C_{18}$ aryl group or a cyclic group with 4–12 carbon atoms in which the ring of the cyclic group also contains one or more heteroatoms, for example nitrogen. Alkyl groups include, among others, methyl, ethyl, isopropyl, tert-butyl, cyclopentyl, cyclohexyl or cyclooctyl. Exemplary cyclic groups containing heteroatoms include, among others, 6-methyl-2-pyridyl and 4,6-dimethyl-2-pyridyl.

Aryl groups include, for example, naphthyl, phenyl, benzyl, cumenyl, mesityl, tolyl and xylyl. The organic group can be substituted, for example, with halogen atoms, for example Cl, Br or F, or with $C_1$–$C_6$ alkyl, $C_6$–$C_{18}$ aryl, $C_1$–$C_6$ alkoxy, carboxy, carbalkoxy, acyl, trihalogenmethyl, cyano, dialkylamino, sulphonylalkyl or alkanoyloxy groups. Substituents can be groups with electron withdrawing or electron donating properties.

Monodentate phosphine ligands include, for instance, tri-p-tolylphosphine, tri-p-methoxyphenyl-phosphine, diphenylpentylphosphine or dimethylphenyl-phosphine. Preferably triphenylphosphine is used because this compound is readily available.

Preferaly multidentate phosphine ligands are used, represented by the following general formula (4):

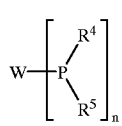

(4)

wherein n is 2–6, W is a multivalent (valency equals n) organic bridging group with 2 to 40 carbon atoms and $R^4$ and $R^5$ each individually represent an optionally substituted organic group. By preference, n is 2 in formula (4). Organic groups for $R^4$ and $R^5$ can be the same as described above for $R^1$, $R^2$ and $R^3$. Furthermore $R^1$ and $R^2$ can form one divalent organic group, for example a diaryl group or a $C_2$–$C_{20}$ alkenyl group. An exemplary alkenyl group is butenyl. Examples of diaryl groups include diphenyl and dinaphthyl groups. The substituents for the organic groups in formula (4) can be the same as described above for the monodentate phosphine ligands.

Preferably the multidentate phosphine ligand is a bidentate phosphine ligand (n=2) according to formula (5).

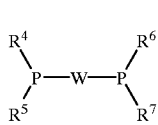

(5)

in which $R^6$ and $R^7$ can be the same as described above for $R^4$ and $R^5$. Preferably one or more of groups $R^4$, $R^5$, $R^6$ and/or $R^7$ are aliphatic groups. Examples of possible aliphatic and aryl groups are described above for $R^1$, $R^2$, $R^3$, $R^4$ and $R^5$.

Divalent organic bridging groups include $C_2$–$C_{10}$ alkylidene groups, for example ethylene, trimethylene, tetramethylene, pentamethylene or trans-1, 2-cyclobutene; and $C_6$–$C_{20}$ divalent arylgroups such as, for example, dinapthyl or diphenyl. Preferably the number of carbon atoms in the shortest chain connecting the phosphorus atoms is three or four. In this chain one non-terminal hetero atom may be present, for example oxygen or sulphur. A class of divalent bridging group W having 4 carbon atoms in the shortest chain connecting the two phosphorus atoms is illustrated by formula (6)

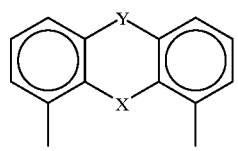

(6)

in which X is a -O- or -S- atom and Y is a group which contains oxygen, sulphur, nitrogen, silicon or a carbon atom or combinations of these atoms. Examples of bidentate phosphine ligands having a bridge as described by formula (6) are described in WO-A-9530680 which document is incorporated herein by reference.

The bidentate phosphine ligands include, among others, 1,3-bis(diphenylphosphino)propane, 1,4-bis(diphenylphosphino)butane, 2,3-dimethyl-1,4-bis(diphenylphosphino)butane, 1,4-bis(n-butylphenylphosphino) butane, 1,4-bis(dicyclohexyl-phosphino)butane, 1,4-bis (cyclohexylphenylphosphino) butane, 1,3-bis(di-p-tolylphosphino) propane, 1,4-bis(di-p-methoxyphenylphosphino)butane, 2,3-bis(diphenylphosphino)-2-butene, 1,3-bis(diphenyl-phosphino)-2-oxopropane, 2-methyl-2-(methyldiphenyl-phosphino)-1, 3-bis(diphenyl-phosphino)propane, 2,2'-bis(diphenylphosphino)biphenyl, 2,3-bis(diphenyl-phosphino) naphthalene, 1,2-bis(diphenylphosphino)-cyclohexane, 2,2-dimethyl-4,5-bis(diphenylphosphino)-dioxolane, 2,3-o-isopropylidene-2,3-dihydroxy-1,4-bis(diphenylphosphino)-butane (DIOP), trans-1,2-bis(di(m-methylphenyl)-phosphinemethyl)cyclobutane, trans-[(bicyclo[2.2.1]-heptane-2,3-diyl)bis(methylene)]-bis[diphenylphosphine], trans-[(bicyclo[2.2.2]octane-2,3-diyl)bis(methylene)]-bis[diphenylphosphine], trans-1,2-bis(diphenylphosphino-methyl) cyclobutane (DPMCB), trans-1,2-bis(diphenyl-phosphinemethyl)trans-3,4-bis(phenyl)-cyclobutane and 2,2'-bis(diphenylphosphino)-1,1'-binapthyl (BINAP).

Group W may also be a divalent bis(n-cyclopentadienyl) coordination group of a transition metal. The transition metal can be selected from among Fe, Zr, Co, Ni, Ti, Ru and W. Preferably Fe is used, in which case the bridging groups is referred to as a ferrocenyl group.

Bidentate phosphine ligands with a ferrocenyl bridging group include, for instance, 1,1'-bis(diphenyl-phosphino) ferrocene, 1,1'-bis(diisobutyl-phosphino) ferrocene, 1,1'-bis(diisopropylphosphino)-ferrocene, 1,1'-bis(dicyclohexylphosphino)-ferrocene, 1,1'-bis(isopropyl-cyclohexylphosphino)-ferrocene, 1,1-bis(di-t-butylphosphino)ferrocene, 1,1'-bis(isopropylphenylphosphino)-ferrocene.

The molar ratio of phosphine ligand to palladium depends on the specific phosphine ligand used in the process according to the invention. This ratio will preferably be between 1:1 and 100:1. For multidentate phosphine ligands this ratio is preferably between 1:1 and 10:1. When using monodentate phosphine ligands this ratio is preferably greater than 5:1. When this ratio is too high the catalytic effect of the catalyst system is weaker and by-products such as vinyl cyclohexene and high-molecular weight products may form. Both multidentate and monodentate phosphine ligands can be simultaneously present during the carbonylation.

All inert solvents are in principle suitable as an additional solvent, although it is also possible to use an excess of one of the reactants or (by-) products in such an amount that a suitable liquid phase is formed. Examples of (by-) products are $C_9$-esters and other high boiling by-products. Examples of inert solvents are sulphoxides and sulphones, such as for instance, dimethyl sulphoxide, diisopropyl sulphone; aromatic solvents, such as benzene, toluene, xylene; esters, such as methyl acetate, methyl valerate, pentenoate esters and butyrolactone; ketones, such as acetone or methylisobutyl ketone; ethers such as anisole, trioxanone, diphenyl ether and diisopropyl ether; and mixtures of these solvents. Preferably, diphenyl ether is used as additional solvent.

In the process according to the invention it is found the reaction can be performed without the addition of any alcohol corresponding with the ester group of the alkyl or aryl pentenoate. If no additional alcohol is supplied to the process the reaction will generally be performed in the presence of less than 0.01 mol alcohol per mol of butene-1-derivative.

The palladium can be added to the reaction mixture as a heterogeneous palladium compound or as a homogeneous palladium compound. However, homogeneous systems are preferred. Since palladium forms a complex in situ with the phosphine ligand, the choice of the initial Pd compound is in general not critical. Homogeneous palladium compounds include, for instance, palladium salts of, for instance, nitric acid, sulphonic acid, alkane carboxylic acids with not more than 12 carbon atoms or hydrogen halogenides (Cl, Br, I). Metallic palladium can also be used. Exemplary homogeneous palladium compounds include $PdCl_2$, $PdBr_2$, $PdI_2$, $Na_2PdI_4$, $PdI_4$, $PdCl_2(benzonitrile)_2$ and bis(allylpalladium chloride). Another group of suitable halogen-free palladium compounds are palladium complexes such as palladium acetylacetonate $(Pd(acac)_2)$, Pd(II) acetate, palladiumnitrate $Pd(NO_3)_2$, o-tolyl phosphine palladium, and di-palladium-tris-(dibenzylideneacetone)$Pd_2(dba)_3$. An exemplary of a heterogeneous palladium compound is a palladium compound on an ion exchanger such as, for example an ion exchanger containing carboxylic acid groups. Ion exchangers containing carboxylic acid groups are commercially available under the brand names Amberlite IRC 50 and Amberlite IRC 84 (Rohm & Haas). Another heterogeneous catalyst is an immobilized phosphine on carrier catalyst, in which the palladium forms a complex with the immobilized phosphine (phosphine being the ligand of the catalyst system). Carriers include polystyrene, polyacrylamide, silica, alumina, silica-alumina or zeolite support.

The palladium concentration in the reaction mixture is preferably as high as possible because the greater will be the rate of reaction per unit of reactor volume. The upper limit for a homogeneous catalyst system will normally be determined by the solubility of palladium in the reaction mixture and will, for example, depend on the specific palladium compound used as discussed above. This upper limit can easily be determined by one skilled in the art. However, the process according to the invention may also be performed with a homogeneous catalyst system in the presence of solid palladium compounds.

The reaction is preferably performed in the presence of a protonic acid having a pKa between 2–6 measured in water at 18° C. Preferred acids are carboxylic acids having 1 to 30 carbon atoms. These carboxylic acids may be substituted with hydroxy, $C_1$–$C_4$ alkoxy, for example methoxy, amine or halogenide groups, for example Cl, I and Br. Exemplary carboxylic acids are benzoic acid, acetic acid, valeric acid, pentenoic acid, nonanoic acid and butanoic acid. The acid is preferably a sterically hindered carboxylic acid having a pKa of less than 4.5. Exemplary sterically hindered carboxylic acids are sterically hindered benzoic acids, for example 2-fluorobenzoic acid and 2-(trifluormethyl)-benzoic acid, the $C_1$–$C_4$ alkyl substituted benzoic acid, for example 2,6-dimethylbenzoic acid, 2,4,6-trimethyl benzoic acid and hydroxy substituted benzoic acid, for example meta- and parahydroxybenzoic acid and other substituted benzoic acids, for example 2,6-difluorobenzoic acid or 2,4,6-tribromobenzoic acid. Most preferably 2,4,6-trimethylbenzoic acid is used.

The molar ratio of carboxylic acid to palladium is preferably greater than 10:1 in the process according to the invention. Apart from practical considerations, there is no upper limit to this ratio. Because, as explained above, the palladium concentration is preferably as high as possible, this will result in a practical upper limit. Furthermore it has been found that the optimum carboxylic acid to palladium ratio depends on the specific carboxylic acid which is used as co-catalyst. The carboxylic acid may serve as the solvent of the carbonylation reaction.

The temperature is preferably between 25° C. and 200° C. The pressure is not particularly critical and generally ranges between 1 MPa and 100 MPa, although it is preferably greater than 2 MPa. An upper limit is not critical. A very high pressure is disadvantageous because the process equipment will become very expensive. A practical and preferred upper limit is therefore about 10 MPa.

The carbon monoxide can be used in a pure form or diluted with an inert gas such as, for example, nitrogen, rare gases or carbon dioxide. In general, more than 5% hydrogen is undesirable, since this can cause hydrogenation of the butene-derivative under the carbonylation conditions.

Preferably a continuous process is used. An example of reactor system for a continuous process is a series of continuously stirred tank reactors (CSTR) in which the catalyst system, a possible solvent, Compound 1 and carbon monoxide are fed to a first reactor. The various ratios according to the process of the invention can be maintained by controlling the feed rate of the various reactants and catalyst components.

The pentenoic acid derivative will be obtained as a mixture of 2-, 3- and 4-pentenoic acid derivative. Usually first the more volatile compounds present in the mixture obtained in the process according the invention are separated. For example, carbon monoxide will usually be separated by a simple flash operation. Other compounds which are more volatile than the pentenoic acid derivative will comprise any unconverted butene derivative.

The invention is also directed to a process in which the following steps are performed:

(a) butadiene is reacted with ROH in the presence of a catalyst to a mixture of butene-1 and butene-2 derivatives according to formula (1) and (2) respectively:

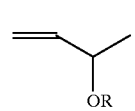

(1)

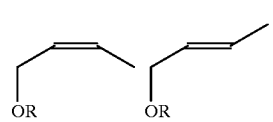

(2)

(b) optionally the butene-1-derivative is separated from the butene-2-derivative and (c) the butene-1-derivative is reacted with carbon monoxide to the pentenoic acid derivative in the presence of the catalyst system comprising palladium, a phosphine ligand and an acid promotor in which the molar ratio of butene-1-derivative to butene-2-derivatives is higher than 4.

Step (a) according to this embodiment of the invention can be performed by generally known processes, for example described in U.S. Pat. No. 4,343,120, U.S. Pat. No. 4,590,300, DE-A-2550902 and EP-A-25240 the complete disclosure of which are incorporated herein by references. Examples of homogeneous catalyst systems comprise bis(1, 5-cyclooctadiene)nickel, 1,2-bis-(diphenylphosphine) ethane, n-butyllithium or 1,2-bis(dialkyl-phosphino) ethane-palladium. Step (a) is preferably performed in the presence of an acid catalyst, and more preferably a heterogeneous acid catalyst. Examples of possible acid catalysts are sulfuric acid, sulfonic acids, for example methane sulfonic acid or trifluoromethane sulfonic acid, trifluoro acetic acid, phosphoric acid, or heterogeneous acid catalysts, for example strongly acidic ion-exchange resins, for example sulphonated polystyrene-divinylbenzene ion-exchange resins.

Specific examples of suitable resins include Amberlite IR 120 H, Amberlite A 252, Amberlite XE 307, Ambelyst 15 H. Amberlyst CSP-2, Dowex SO-X-4, Dowex MSC-14, Duolite C-20, Permutit QH or Chempro C-20 and Nafion (Amberlite, Amberlist, Dowex, Duolite, Permutit, Chempro and Nafion are registered Trade Marks).

Step (a) can be performed in the presence of an additional solvent. Examples of solvents are aromatic solvents, for example benzene, toluene, xylene, dichlorobenzene and non-basic aprotic polar solvent such as described in EP-A-25240. Examples of suitable non-basic aprotic polar solvents are acyclic or cyclic sulphones, sulphoxides, ketones, (poly)ethers, nitromethane and γ-valerolactone. Examples of these compounds are described in more detail in EP-A-25240. Most preferably cyclic sulphones are used, for example sulfolane or alkyl sulfolanes, in which at least one alkyl group having 1–8 carbon atoms is present. Cyclic sulphones are preferred because their high boiling points are advantageous in step (b).

The butadiene may be present in a mixture of butenes and butynes as for example obtained as the $C_4$-cut in a steam cracker.

The molar ratio of nucleophilic compound to butadiene can be up to 20:1. Preferably this ratio is between 1:1 and 6:1.

Step (a) can be performed at mild temperature ranges. Prefered temperature ranges are of 40–200° C.

Step (a) is preferably performed in the liquid phase. The pressure is therefore at least high enough to keep the reactants in the liquid phase. The pressure may be between 0.1–20 MPa and preferably between 2–6 MPa.

The butene derivatives (alkoxy-butenes and aryloxy-butenes) are as a rule less toxic than butadiene. Furthermore butadiene can upon storage/transport give rise to a hazardous polymerization reaction. Therefore it can be advantageous to store or transport the butene derivatives instead of butadiene.

Step (b) can be optionally performed by any known separation method, for example extraction or crystallization. If the molar ratio of the butene-1 derivative to the butene-2 derivatives in the mixture obtained in step (a) is higher than 4 the mixture can be directly used in step (c), after separating the catalyst and preferably any unconverted butadiene. Preferably step (b) is performed by making use of the difference in boiling points of the compounds to be separated. Generally butadiene, butene-1-derivatives, the butene-2-derivatives and the acidic catalyst have boiling points in increasing order.

Step (c) can be performed as described above.

The invention shall be elucidated by the following non-limiting examples.

EXAMPLE I

The following steps (a)–(c) were performed:

(a) In a 5 l autoclave 302 grams of butadiene was reacted with 538 g methanol in 2.4 l toluene (solvent) for 6 hours in the presence of 140 g Amberlist CSP-2 (ionexchanger with acidic groups, Amberlist is a tradename of Rohm & Haas) at 120° C. under a 4 MPa nitrogen atmosphere.

(b) After washing the toluene fraction obtained in step (a) with water, 50 grams of 3-methoxy-1-butene was recovered from the mixture by a batch distillation. The 3-methoxy-1-butene was 98% pure.

(c) A 120 ml mechanically stirred Hastelloy-C autoclave was charged with 0.056 g (0.25 mmole) of palladium acetate, 0.533 g (1.25 mmole) of bis (diphenylphosphino)butane, 0.82 g (5 mmole) of 2,4, 6,-trimethylbenzoic acid, 0.5 g ortho-dichlorobenzene (ODCB, GC internal standard) and 33 g of toluene solvent. The solution was heated to a temperature of 140° C. under an initial pressure of 2.07 MPa (300 psi). The reaction was initiated by injecting a solution of 4.3 g (50 mmole) of 3-methoxy-1-butene in 5 g toluene and adjusting the total pressure to 5.17 MPa (750 psi). Carbon monoxide was continuously fed to the autoclave from a reservoir so as to maintain the total pressure constant at 5.17 MPa (750 psi). Samples were removed at intervals for GC analysis. After 1 hour 88% of the 3-methoxy-1-butene charged was converted to methyl-3-pentenoate (M3P; cis and trans isomers) with a selectivity of 95.2%. The selectivity to methyl-2-pentenoate (M2P; predominantly trans isomer) was 2.9%. The first order rate constant for the formation of M3P was 2.11 $hr^{-1}$, corresponding to a turnover of 305 moles M3P per mole of palladium per hour.

EXAMPLE II 5 grams of the 3-methoxy-1-butene as obtained in step (b) of Example I was injected into a 160 ml Hasteloy C autoclave containing 0.064 grams of palladium acetate, 0.62 grams of bis(diphenylphosphino)propane, 0.96 grams of 2,4,6-trimethylbenzoic acid and 53 grams of diphenylether (solvent). The pressure was adjusted to 5 MPa by adding carbon monoxide. After stirring the mixture for 1 hour at 140° C., the conversion of 3-methoxy-1-butene was 47% with a selectivity of >98% to methylpentenoate. The selectivity to methyl-2-pentenoate was 1.8%.

COMPARATIVE EXPERIMENT A

Step (c) of example I was repeated except that the 3-methoxy-1-butene was replaced by a mixture of methoxy-butenes containing 70% 1-methoxy-2-butene and 30% 3-methoxy-l-butene. After 1 hour the conversion to M3P was only 31%, the selectivity to M3P was 94.5% and the selectivity to M2P was 2.6%. After 6 hours the conversion to M3P was 88%, the selectivity to M3P was 92.3% and the selectivity to M2P was 5.8%. The first order rate constant for the formation of M3P was 0.37 $hr^{-1}$, corresponding to a turnover frequency of 54 moles M3P per mole of palladium per hour.

COMPARATIVE EXPERIMENT B

The experiment in Example III was repeated except that the 3-methoxy-1-butene was replaced by a equivalent molar amount of butadiene and methanol (1/1) injected from a high pressure pump. After 1 hour the conversion to M3P was 55%, the selectivity to M3P was 97% and the selectivity to M2P was 1.2%. After 2 hours the conversion to M3P was 86.4%, the selectivity to M3P was 96.4% and the selectivity to M2P was 2.4%. The first order rate constant for the formation of M3P was 1.00 hr$^{-1}$, corresponding to a turnover frequency of 144 moles M3P per mole of palladium per hour.

EXAMPLES III–VIII

A 25 ml glass lined pressure vessel was charged with 2.5 ml of a solution containing 4.3 g (50 mmol) 3-methoxy-1-butene, 0.034 g (0.15 mmol) of palladium acetate, 0.75 mmole of bidentate phosphine ligand (see Table 1), 0.495 g (3 mmole) 2,4,6,-trimethylbenzoic acid and 0.5 g of o-dichlorobenzene (internal GC standard) in 50 ml toluene. The pressure vessel was freed from air by purging first with nitrogen (twice) and then with CO (twice). The vessel was then pressurized to 3.45 MPa (500 psi) CO and heated to 140° C. with agitation for 4 hours. The pressure at 140° C. was maintained at 5.17 MPa (750 psi). After 4 hours the heat was shut off and the pressure vessel was allowed to cool to room temperature. The excess gases were vented and the products were analyzed by GC. The results for the ligands indicated are presented in Table 1.

TABLE 1

| Example | Ligand | Conversion | Selectivity |
|---|---|---|---|
| III (15-2) | 1,3-bis(cyclohexyl-phenylphosphino)-propane | 32.6 | 94.9 |
| IV (14-4) | 1,5-bis(diphenyl-phosphino)pentane | 24.7 | 92.3 |
| VI (15-3) | 1,4-bis(dicyclo-hexylphosphino)butane | 69.5 | 95.0 |
| VII (19-5) | 2,3-o-isopropylidene-2,3-dihydroxy-1,4-bis(diphenylphosphino)-butane (DIOP) | 29.2 | 95.8 |
| VIII (14-6) | bis(diphenyl-phosphino)ferrocene | 52.8 | 99.3 |

What is claimed is:

1. Process for the preparation of an alkyl pentenoate respectively an aryl pentenoate by contacting an alkoxy-butene respectively an aryloxy-butene compound with carbon monoxide in the presence of a catalyst system comprising palladium, a phosphorus ligand and an acid promotor, wherein the molar ratio of 3-alkoxy-1-butene to 1-alkoxy-2-butene, respectively the molar ratio of 3-aryloxy-1-butene to 1-aryloxy-2-butene, is higher than 4.

2. Process according to claim 1, wherein the ligand is a phosphine ligand according to

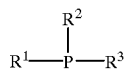

in which $R^1$, $R^2$ and $R^3$ each individually represent an optionally substituted organic group, which group is a $C_1$–$C_{20}$ alkyl group, a $C_6$–$C_{18}$, aryl group or a cyclic group with 4–12 carbon atoms in which the ring of the cyclic group also contains one or more heteroatoms.

3. Process according to claim 1, wherein the ligand is a phosphine ligand according to

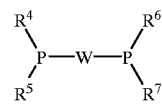

in which $R^4$, $R^5$, $R^6$ and $R^7$ each individually represent an optionally substituted organic group, which groups $R^4$–$R^7$ are optionally substituted $C_1$–$C_{20}$ (cyclo)alkyl groups, $C_6$–$C_{18}$ aryl groups or cyclic groups with 4–12 carbon atoms in which the ring of the cyclic group contains one or more hetero atoms, or in which $R^4$ and $R^5$ and/or $R^6$ and $R^7$ are one divalent organic alkenyl group or diaryl group and in which W is an organic bridging group having 2 to 40 carbon atoms.

4. Process according to claim 3, wherein the number of carbon atoms in the shortest chain connecting the phoshorus atoms is four, in which this chain may contain one heteroatom.

5. Process according to any one of claims 1–4, wherein the acid promotor is a carboxylic acid having a pKa between 2–6 measured in water of 18° C.

6. Process according to any one of claims 1–4, wherein the aryloxy group of the aryloxy-butene has 6–20 carbon atoms.

7. Process according to any one of claims 1–4, wherein the alkoxy group of the alkoxy-butene has 1–20 carbon atoms.

8. Process according to claim 7, wherein the alkoxy group is methoxy or ethoxy.

9. Process to prepare pentenoic acid derivative starting from butadiene, carbon monoxide and a nucleophilic compound, ROH, having a removable hydrogen atom using a catalyst system comprising palladium and a phosphine ligand, wherein the following steps are performed:
   (a) butadiene is reacted with ROH in the presence of an acidic catalyst to a mixture of butene-1 and butene-2 derivatives according to formula (1) and (2) respectively:

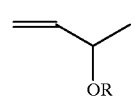

(1)

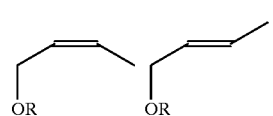

(2)

(b) optionally the butene-1-derivative is separated from the butene-2-derivative and
   (c) the butene-1-derivative is reacted with carbon monoxide to the pentenoic acid derivative in the presence of the catalyst system comprising palladium, a phosphine ligand and an acid promotor in which the molar ratio of butene-l-derivative to the butene-2-derivatives is higher than 4.

10. Process according to claim 9, wherein R is an aliphatic, cycloaliphatic or an aromatic group having 1 to 20 carbon atoms.

11. Process according to claim 10, wherein R is a methyl or ethyl group.

12. Process according to claims 9, 10 or 11, wherein the acidic catalyst used in step (a) is a strongly acidic ion-exchange resin.

13. Process according to claims 9, 10 or 11, wherein the molar ratio of nucleophilic compound and butadiene is between 1:1 and 6:1.

14. Process according to claims 9, 10 or 11, wherein the separation in step (b) is performed by one or more distillation steps.

15. Process according to claims 9, 10 or 11, wherein the phosphine ligand compound of the catalyst system used is a compound according to

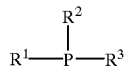

in which $R^1$, $R^2$ and $R^3$ each individually represent an optionally substituted organic group, which group is a $C_1$–$C_{20}$ alkyl group, a $C_6$–$C_{18}$ aryl group or a cyclic group with 4–12 carbon atoms in which the ring of the cyclic group also contains one or more heteroatoms.

16. Process according to any one of claims 9, 10 or 11, wherein the phosphine ligand compound of the catalyst system is a compound according to

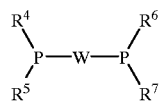

in which $R^4$, $R^5$, $R^6$ and $R^7$ each individually represent an optionally substituted organic group, which groups $R^4$–$R^7$ are optionally substituted $C_1$–$C_{20}$ (cyclo)alkyl groups, $C_6$–$C_{18}$ aryl groups or cyclic groups with 4–12 carbon atoms in which the ring contains one or more hetero atoms, or in which $R^4$ and $R^5$ and/or $R^6$ and $R^7$ are one divalent organic alkenyl group or diaryl group and in which W is an organic bridging group having 2 to 40 carbon atoms.

17. Process according to claim 16, wherein the number of carbon atoms in the shortest chain connecting the phoshorus atoms is four, in which this chain may contain one heteroatom.

18. Process according to any one of claims 9, 10 or 11, wherein the acid promotor is a carboxylic acid having a pKa between 2–6 measured in water of 18° C.

* * * * *